United States Patent [19]

Yoneyama et al.

[11] 4,272,615
[45] Jun. 9, 1981

[54] PHOTOGRAPHIC LIGHT-SENSITIVE ANTISTATIC CONTAINING MATERIAL

[75] Inventors: Masakazu Yoneyama; Shinzo Kishimoto, both of Minami-ashigara; Yasuhiro Nakayama, Fujinomiya, all of Japan

[73] Assignee: Fuji Photo Film Co., Ltd., Minami-ashigara, Japan

[21] Appl. No.: 54,492

[22] Filed: Jul. 3, 1979

[30] Foreign Application Priority Data

Jul. 3, 1978 [JP] Japan ................... 53-80657

[51] Int. Cl.³ .............................. G03C 1/78
[52] U.S. Cl. ........................ 430/527; 430/631
[58] Field of Search ............. 96/87 R, 114.2; 260/DIG. 15; 430/527, 631

[56] References Cited

U.S. PATENT DOCUMENTS 3,884,699  5/1975  Cavallo et al. ................... 96/87 A
4,013,696  3/1977  Babbitt et al. ................... 96/87 A
4,050,940  9/1977  Habu et al. ...................... 96/87 A
4,112,206  9/1978  Wingrave ................... 260/DIG. 15

FOREIGN PATENT DOCUMENTS 52-41182  3/1977  Japan.

Primary Examiner—Jack P. Brammer
Attorney, Agent, or Firm—Sughrue, Rothwell, Mion, Zinn and Macpeak

[57] ABSTRACT

A photographic light-sensitive material containing in at least one layer a compound represented by the following formula:

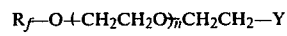

$$R_f-O+CH_2CH_2O)_nCH_2CH_2-Y$$

wherein $R_f$ represents a perfluoroalkenyl group containing 3 to 12 carbon atoms, n represents an integer 3 to 50, and Y represents a hydroxy group or an organic residue containing 1 to 18 carbon atoms.

10 Claims, No Drawings

PHOTOGRAPHIC LIGHT-SENSITIVE ANTISTATIC CONTAINING MATERIAL

BACKGROUND OF THE INVENTION

1. Field of the Invention

The present invention relates to a silver halide photographic light-sensitive material having improved antistatic property and more particularly to a photographic light-sensitive material having an improved antistatic property without detrimentally influencing photographic properties.

2. Description of the Prior Art

Photographic light-sensitive materials generally comprise an electrically insulative support and one or more photographic layers. Electrostatic charges often accumulate during the production of photographic light-sensitive materials or upon use thereof generated as the light-sensitive material contacts surfaces such as a roller or guide surface or the surface of an adjacent roll of film during wind up. This accumulation of electrostatic charge can result in many problems, the most serious of which is the formation of spots or tree-like or fur-like lines (so-called static marks) upon developement of the exposed photographic film. These marks are formed by discharge of the accumulated electrostatic charge before development. Static marks seriously spoil the commercial value of photographic films and, in an extreme case, render the film useless. For example, it can readily be understood that such static marks on X-ray films for medical or industrial use could lead to an incorrect diagnosis. This phenomenon presents an extremely difficult problem because it is only observed after development. In addition, the accumulated electrostatic charge can cause secondary problems such as adhesion of dust to the film surface and non-uniform coating.

As explained above, such electrostatic charges often accumulate upon production and use of photographic light-sensitive materials. In the production steps, the electrostatic charge develops due to contact friction between photographic films and rollers or separation of the support surface from the emulsion surface during the film-winding or film-unwinding. With finished products, it develops due to separation of a base surface and an emulsion surface from each other upon winding up and changing films or contact or separation of X-ray films with or from mechanical members or fluorescent brightening paper in an automatic photographing machine.

Static marks in photographic light-sensitive materials formed by the accumulated electrostatic charge become more serious as the sensitivity of the photographic light-sensitive material increases and as the processing speed increases. Particularly, photographic light-sensitive materials have recently often been subjected to severe processing conditions to increase sensitivity, high-speed coating, high speed photographing, high speed automatic processing, etc., and hence static marks occur more readily.

The best solution to the static electricity problem is to increase the conductivity of the photographic materials, thus allowing the charge to dissipate in a short time prior to discharge of the accumulated charge.

Thus, attempts have been made to improve the conductivity of the support and various surface-coating layers of photographic light-sensitive materials using various hygroscopic materials, water-soluble inorganic salts, certain kinds of surfactants, polymers, etc. Thus, the polymers described in, for example, U.S. Pat. Nos. 2,882,157, 2,972,535, 3,062,785, 3,262,807, 3,514,291, 3,615,531, 3,753,716, 3,938,999, etc., the surfactants described in, for example, U.S. Pat. Nos. 2,982,651, 3,428,456, 3,457,076, 3,454,625, 3,552,972, 3,655,387, etc., and zinc oxide, semi-conductors, colloidal silica, etc., described in, for example, U.S. Pat. Nos. 3,062,700, 3,245,833, and 3,525,621, have been used to combat the static mark problems.

However, the properties of these materials are so specific and depend so much upon the kind of the film support and the photographic composition, that while they provide good results with some particular film supports and photographic layers, they are completely useless for preventing development of static electricity with other film supports and photographic layers and, in some cases, exert a detrimental influence on the photographic properties. In particular, it has been extremely difficult to prevent development of electrostatic charges on a hydrophilic colloidal layer and, in many cases, there results an insufficient reduction in surface resistance under low humidity or adhesion problems arise between the photographic light-sensitive materials or between a photographic light-sensitive material and other surfaces under a high temperature and a high humidity conditions.

On the other hand, some materials cannot be used to increase conductivity due to their adverse effect on the photographic properties such as sensitivity of photographic emulsions, fog, graininess, sharpness, etc., in spite of their excellent antistatic effect. For example, polyethylene oxide series compounds, generally known to have an antistatic effect, often exert a detrimental influence on photographic properties such as an increase of fog, desensitization, deterioration of graininess, etc.

In particular, it has been difficult to effectively impart an antistatic property to light-sensitive materials having photographic emulsions on both sides of the support such as X-ray sensitive materials for medical use without detrimentally influencing the photographic properties. As explained above, application of an antistatic agent to photographic light-sensitive materials is extremely complex and the use of the agent is often restricted.

SUMMARY OF THE INVENTION

An object of the present invention is to provide a photographic light-sensitive material having antistatic property.

Another object of the present invention is to provide a high speed photographic light-sensitive material exhibiting low surface resistance under low humidity (about 25% RH) and having an antistatic property.

A further object of the present invention is to provide a method for effectively making a photographic light-sensitive material antistatic without detrimentally influencing photographic properties (for example, sensitivity, fog, graininess, sharpness, etc.).

Still a further object of the present invention is to provide a photographic light-sensitive material having an improved film surface adhesion resistance.

It has been found that these objects can be attained by incorporating a polyethylene oxide compound having a perfluoroalkenyl group represented by the following formula in at least one layer of a photographic material:

$R_f\text{—}O\text{+}CH_2CH_2O\text{)}_n CH_2CH_2\text{—}Y$ wherein $R_f$ represents a perfluoroalkenyl group containing 3 to 12 and preferably 3 to 9 carbon atoms, n is an integer of 3 to 50 and preferably 5 to 20, and Y represents a hydroxy group or an organic residue containing 1 to 18 carbon atoms and preferably 1 to 10 carbon atoms.

DETAILED DESCRIPTION OF THE INVENTION

The photographic light-sensitive material provided with an antistatic property in accordance with the present invention is characterized in that a polyethylene oxide compound containing a perfluoroalkenyl group present in a layer constituting the photographic light-sensitive material.

Y in the above formula includes a hydroxy group and any organic residue containing 1 to 18 carbon atoms and may be a straight chain, branched chain, cyclic, saturated or unsaturated organic residue. That is, Y represents the residue of any organic compound that has an active hydrogen atom capable of entering an addition reaction with ethylene oxide. For example, Y includes organic residues such as an alkoxy group, an alkenyloxy group, a phenoxy group, a naphthoxy group, an alkylphenoxy group, an alkylnaphthoxy group, an alkylamino group, an alkenylamino group, an alkylthio group, a perfluoroalkenyl group, etc., preferably an alkoxy group containing 1 to 10 carbon atoms, and residues formed by adding propylene oxide to the above-described organic residues, a representative example of Y is $RO(C_3H_6O)_n$—wherein R represents an alkyl group, etc., and n represents 1 to 20.

Examples of the perfluoroalkenyl group represented by $R_f$ include a perfluoropropenyl group, a perfluorohexenyl group, a perfluorononenyl group, a perfluorododecenyl group, etc.

Specific examples of the typical compounds to be used in the present invention are illustrated below. The present invention, however, is not limited to the use of these compounds.

$C_3F_5O(CH_2CH_2O)_{20}C_{12}H_{25}$     1.

$C_3F_5O(CH_2CH_2O)_5C_3F_5$     2.

$C_6F_{11}O(CH_2CH_2O)_{10}C_4H_9$     3.

$C_6F_{11}O(CH_2CH_2O)_{20}C_6H_{13}$     4.

$C_6F_{11}O(CH_2CH_2O)_7CH_3$     5.

$C_9F_{17}O(CH_2CH_2O)_{20}CH_3$     6.

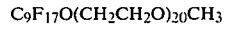     7.

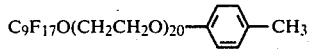     8.

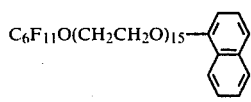     9.

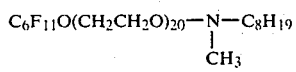     10.

—continued $C_6F_{11}O(CH_2CH_2O)_{40}\text{—}C_{18}H_{35}$     11.

$C_9F_{17}O(CH_2CH_2O)_{10}\text{—}H$     12.

$C_{12}F_{23}O(CH_2CH_2O)_{50}\text{—}CH_3$     13.

$C_6F_{11}O(CH_2CH_2O)_{20}(\underset{\underset{CH_3}{|}}{C}HCH_2O)_5CH_3$     14.

Specific chemical structures of the perfluoroalkenyl groups are, for example, as follows:

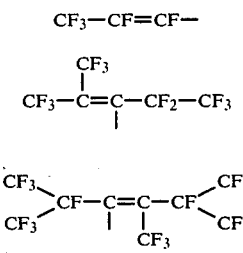

That is, they are a perfluoropropenyl group, the dimer, trimer, tetramer, or the like thereof.

The compounds used in the present invention can readily be synthesized according to, for example, Japanese Patent Application (OPI) No. 41182/77 (The term "OPI" as used herein refers to a "published unexamined Japanese patent application").

The compounds used in the present invention can be synthesized by the dehydrofluorinating condensation between a perfluoroalkane and a hydroxy compound having a polyoxyethylene chain. The reaction may be carried out in the presence of suitable deoxidizing agents such as potassium carbonate in a reaction solvent such as acetone, methyl ethyl ketone, etc., at about room temperature to 40° C.

Synthesis of Compound 6

117.4 g (0.1 mol) of polyoxyethylene methyl ether (n=20) was dissolved in 200 ml of acetone and 17.3 g (0.125 mol) of potassium carbonate was added to the solution. Then 56.3 g (0.125 mol) of perfluorononene was added dropwise to the solution at room temperature while stirring. After stirring at room temperature for 7 hours, the reaction mixture was filtered. The solvents and the excess starting materials present in the mixture were removed by distillation from the filtrate. The filtrate thus-treated was extracted with acetate in order to remove inorganic salts. Concentration and drying of the filtrate yielded 137 g (yield: 85%) of the objective compound.

The compounds of the present invention are added to at least one of the layers constituting the photographic light-sensitive material such as a silver halide emulsion layer, a surface-protecting layer, an interlayer, a backing layer, etc. From the standpoint of preventing static marks from occurring during the manufacture of the photographic material, it is advantageous to incorporate the polyethylene oxide compounds of the present invention in any layer of a photographic light-sensitive material which encounters a significant amount of contact with guide surfaces, rollers, etc., during manufacture and is thus susceptible to static charge accumulation. In particular, addition to a surface layer such as a surface-protecting layer and a backing layer is preferable.

In applying the compound of the present invention to a photographic light-sensitive material, the compound is dissolved in water, an organic solvent (e.g., methanol, isopropanol, acetone, etc.), or the mixture thereof, and added to a coating solution of a surface-protecting layer, a backing layer, or the like, followed by coating by dip-coating, air knife-coating, or extrusion coating using a hopper described in U.S. Pat. No. 2,681,294. Alternatively, two or more layers may be coated at the same time according to methods described in U.S. Pat. Nos. 3,508,947, 2,941,898, 3,526,528, etc., or the material may be dipped in an antistatic agent solution. If necessary, an antistatic solution containing the compound of the present invention is applied to the protective layer.

The compound of the present invention is used in an amount of about 0.005 to 20 g and particularly desirably about 0.01 to 0.5 g per square meter of a photographic film. However, the amount varies depending upon the kind of photographic film base used, the photographic composition, form, and coating method.

As the materials used as the support for the light-sensitive material of the present invention, there are illustrated, for example, a cellulose nitrate film, a cellulose acetate film, a cellulose acetate butyrate film, a cellulose acetate propionate film, a polystyrene film, a polyethylene terephthalate film, a polycarbonate film, the laminate thereof, etc. More particularly, there are illustrated papers coated or laminated with baryta or an α-olefin polymer, in particular, a polymer of α-olefin containing 2 to 10 carbon atoms such as polyethylene, polypropylene, ethylene-butene copolymer, etc.

Transparent or opaque supports may be used depending upon the end-use of the light-sensitive materials. In the case of transparent supports, not only colorless but transparent supports colored by adding dyes or pigments can be used.

Where the adhesion between the support and the photographic emulsion layer is insufficient, a subbing layer may be provided as an adhesive layer having adhesiveness for both the support and the photographic emulsion layer. Also, in order to further improve the adhesion property, the surface of the support may be subjected to conventional preliminary processings such as corona discharge, irradiation with ultraviolet rays, flame treatment, etc.

The layers constituting photographic light-sensitive material of the present invention can contain the following binders. For example, as hydrophilic colloids, there are illustrated proteins (e.g., gelatin, colloidal albumin, casein, etc.), cellulose derivatives (e.g., carboxymethyl cellulose, hydroxyethyl cellulose, etc.), sugar derivatives (e.g., agar-agar, sodium alginate, starch derivatives, etc.), synthetic hydrophilic colloid (e.g., polyvinyl alcohol, poly-N-vinyl pyrrolidone, polyacrylic acid copolymer, polyacrylamide, the derivative or partially hydrolyzed product thereof, etc.). If necessary, a mixture of two or more of these colloids is used. Of these, the most generally used is gelatin. Gelatin as used herein means so-called lime-processed gelatin, acid-processed gelatin, and enzyme-processed gelatin. Gelatin can be replaced partially or wholly by a synthetic high molecular material, by a so-called gelatin derivative (prepared by processing and modifying gelatin with a reagent having a group capable of reacting with the functional groups contained in the gelatin molecule (i.e., amino groups, imino groups, hydroxy groups or carboxy groups)), or by a graft polymer prepared by grafting a molecular chain of other high molecular material.

The silver halide emulsion used in the present invention is usually prepared by mixing a solution of a water-soluble silver salt (e.g., silver nitrate, etc.) with a solution of water-soluble halide (e.g., potassium bromide, etc.) in the presence of a solution of a water-soluble high polymer such as gelatin. As the silver halide, mixed silver halides such as silver chlorobromide, silver bromoiodide, silver chlorobromoiodide, etc., can be used as well as silver chloride and silver bromide. These silver halide grains are prepared according to conventional processes. Of course, they are usefully prepared by a so-called single or double jet process, controlled double jet process, or the like. These photographic emulsions are also described in T. H. James & C. E. K. Mees, *The Theory of the Photographic Process*, 3rd Ed. (published by Macmillan Co.), P. Grafkides, *Chimie Photographique* (published by Paul Montel), or the like, and can be prepared according to various processes commonly known, such as an ammoniacal process, a neutral process, an acidic process, etc.

The thus-prepared silver halide grains can be heat-treated in the presence of a chemical sensitizing agent (for example, sodium thiosulfate, N,N,N,'-trimethylthiourea, monovalent gold thiocyanate complex, monovalent gold thiosulfato complex, stannous chloride, hexamethylenetetramine, etc.) to raise sensitivity without making the grain coarse.

The present invention is particularly suitable for use in conjunction with high speed photographic light-sensitive material. The term "high speed photographic light-sensitive material" used herein includes X-ray sensitive materials, high speed black-and-white sensitive materials (ASA: more than 100) and high speed color sensitive materials (ASA: more than 64). Examples of suitable halogen composition of a silver halide emulsion include AgBrClI ($Br \geq 70$ mol%, 1 mol% $< I \leq 10$ mol% and 0 mol% $\leq Cl \leq 30$ mol%), preferably AgBrI ($Br \geq 90$ mol% and 1 mol% $< I \leq 10$ mol%).

The photographic emulsion can be subjected, if necessary, to spectral sensitization or supersensitization by using polymethine sensitizing dyes (e.g., cyanine, merocyanine, carbocyanine, etc.), alone or in combination, or in further combination with styryl dyes or the like.

To the photographic emulsion of the light-sensitive material of the present invention can be added various compounds in order to prevent reduction in sensitivity and formation of fog in the production step, storage or during processing of the light-sensitive material. As such compounds, there have been long known many compounds such as heterocyclic compounds including 4-hydroxy-6-methyl-1,3,3a,7-tetrazaindene, 3-methylbenzothiazole and 1-phenyl-5-mercaptotetrazole, mercury-containing compounds, mercapto compounds, metal salts, and the like. Some examples of suitable compounds are described in T. H. James & C. E. K. Mees, *The Theory of the Photographic Process* (3rd Ed., 1966, published by Macmillan Co.) citing original literature.

In the case of using the silver halide photographic emulsion for a color photographic light-sensitive materials, couplers may be incorporated in silver halide emulsion layers. As such couplers, 4-equivalent diketomethylene yellow couplers and 2-equivalent diketomethylene yellow couplers such as the compounds described in U.S. Pat. Nos. 3,227,157, 3,408,194, 3,551,155, Japanese Patent Application (OPI) Nos. 26133/72, 66836/73, etc.; 4-equivalent and 2-equivalent pyrazolone magenta couplers and indazolone magenta couplers such as the compounds described in U.S. Pat. Nos. 2,600,788, 3,214,437, 3,476,560, Japanese Patent Application (OPI) No. 26133/72, etc.; α-naphtholic cyan couplers and phenolic cyan couplers such as the compounds described in U.S. Pat. Nos. 2,474,293, 3,311,476, 3,481,741, etc., are used. In addition, couplers capable of releasing a development inhibitor described in U.S. Pat. Nos. 3,227,554, 3,253,924, 3,379,529, 3,617,291, 3,770,436, etc., can be used.

The silver halide emulsion layers and other hydrophilic layers in the photographic light-sensitive material of the present invention can be hardened with various organic or inorganic hardeners (alone or in combination).

As typical examples of the hardeners, there are illustrated aldehyde compounds such as mucochloric acid, formaldehyde, trimethylolmelamine, glyoxal, 2,3-dihydroxy-1,4-dioxane, 2,3 dihydroxy-5-methyl-1,4-dioxane, succinaldehyde, glutaraldehyde, etc.; active vinyl compounds such as divinylsulfone, methylenebismaleimide, 1,3,5-triacryloylhexahydro-s-triazine, 1,3,5-trivinylsulfonyl-hexahydro-s-triazine bis(vinylsulfonylmethyl) ether, 1,3-bis(vinylsulfonylmethyl)propanol-2, bis(α-vinylsulfonylacetamido)ethane, etc.; active halogen compounds such as 2,4-dichloro-6-hydroxy-s-triazine sodium salt, 2,4-dichloro-6-methoxy-s-triazine, etc.; ethyleneimine compounds such as 2,4,6-triethyleneimino-s-triazine, etc.; and the like.

To the layers constituting the photographic material of the present invention may be added surface active agents alone or in combination. They are used as coating aids but, in some cases, they are applied for other purposes, e.g., for the improvement of emulsion dispersion, sensitization, and other photographic properties, and adjustment of charging properties.

These surface active agents are classified into the following groups: natural surface active agents such as saponin; nonionic surface active agents such as polyalkylene oxide surfactants, glycerin surfactants, glycidol surfactants, etc.; cationic surface active agents such as higher alkylamines, quaternary ammonium salts, heterocyclic compounds (e.g., pyridine, etc.), phosphonium compounds, sulfonium compounds, etc.; anionic surface active agents having an acidic group such as a carboxylic acid group, a sulfonic acid group, a phosphoric acid group, a sulfuric ester group, a phosphoric acid ester group, etc.; and amphoteric surface active agents such as aminoacids, aminosulfonic acids, aminoalcohol sulfuric or phosphoric esters, etc.

Examples of suitable surface active agents are described, in part, in patents such as U.S. Pat. Nos. 2,271,623 2,240,472, 2,288,226, 2,739,891, 3,068,101, 3,158,484, 3,201,253, 3,210,191, 3,294,540, 3,415,649, 3,441,413, 3,442,654, 3,475,174, 3,545,974, 3,666,478, 3,507,660, British Pat. No. 1,198,450, etc., and books such as Ryohei Oda et al, *Synthesis and Application of Surface Active Agents* (Maki Shoten, 1964), A. W. Perry, *Surface Active Agents* (Interscience Publication Inc., 1958), J. P. Sisley, *Encyclopedia of Surface Active Agents*, Vol. 2 (Chemical Publish Company, 1964), and the like.

The photographic light sensitive material of the present invention can contain in the light-sensitive material-constituting layers thereof modified silicone and the like lubricating compositions such as those described in U.S. Pat. Nos. 3,079,837, 3,080,317, 3,545,970 and 3,294,537 and Japanese Patent Application No. 129520/77.

The photographic light-sensitive material of the present invention can contain a polymer latex as described in U.S. Pat. Nos. 3,411,911, 3,411,912, Japanese Patent Publication No. 5331/70, etc., and a matting agent such as silica, strontium sulfate, barium sulfate, polymethyl methacrylate, etc.

The photographic material of the present invention provides fewer problems due to static electricity developing during production steps and/or upon use of photographic light-sensitive materials.

For example, formation of static marks caused by contact between the emulsion surface of the photographic light-sensitive material and the back side thereof, contact between the emulsion surfaces, and contact between the photographic light-sensitive material and substances with which the light-sensitive material generally often come into contact, such as rubber, metal, plastics, and fluorescent brightening paper has been remarkably reduced by the practice of the present invention. Surprisingly enough, as will be shown by the following examples, incorporation of the compound of the present invention in an outermost layer of a photographic light-sensitive material results in remarkable reduction in surface resistance with almost no influence on photographic properties.

The present invention will now be described in more detail by the following examples which, however, do not limit the present invention in any way.

EXAMPLE 1

On the sides of about a 175-μ thick polyester support were coated, in sequence, an emulsion layer and a protective layer in an ordinary manner and dried to prepare samples (1) to (8). Compositions of respective layers were as follows.

| Emulsion Layer: about 5 μ thick | |
|---|---|
| Binder: | |
| gelatin | 2.5 g/m² |
| Amount of Coated Silver: | 5 g/m² |
| Silver Halide Composition: | |
| AgI | 1.5 mol % |
| AgBr | 98.5 mol % |
| Hardener: | |
| chromium alum | 0.8 g/100 g gelatin |
| Antifogging Agent: | |
| 1-phenyl-5-mercaptotetrazole | 0.5 g/100 g Ag |
| Protective Layer: about 1 μ thick | |
| Binder: | |
| gelatin | 1.7 g/m² |
| potassium polystyrene-sulfonate (mean molecular weight: about 70,000) | 0.3 g/m² |
| Hardener: | |
| N-oleoyl-N-methyltaurine sodium salt | 7 mg/m² |

Sample (1) comprised only the above-described composition, and samples (2) to (4) respectively contained, in addition to the above-described composition, compounds 1, 5 and 6 of the present invention in the protective layer in an amount of 40 mg/m². For the purpose of comparison, samples (5) to (8) were prepared containing respectively saponin, saccharose monolauric acid ester, polyoxyethylene nonylphenyl ether (n=10), and polyoxyethylene lauryl ether (n=20) in an amount of 40 mg/m² in said protective layer in addition to the above-described composition.

Antistatic properties of these samples were examined as follows.

(1) Measurement of Specific Surface Resistance:

After moisture conditioning of each sample for 2 hours at 25° C. and under 25% RH, the test piece was placed between brass-made electrodes 10 cm in length with an electrode-to-electrode spacing of 0.14 cm (portions in contact with the test piece being made of stainless steel) under the same conditions, followed by measuring the specific surface electricity as one-minute value using an electrometer (TR-8651) made by Takeda Riken Co., Ltd.

(2) Measurement of Static Marks:

After moisture-conditioning, unexposed samples under the same conditions as described above were rubbed with a rubber roller, or nylon roller in a dark room under the same conditions, and developed using the following developer, followed by fixing and washing with water to examine the degree of formation of static marks.

The degree of formation of static marks was rated according to the following four grades:

A: No static marks were observed.
B: Static marks were slightly observed.
C: Static marks were considerably observed.
D: Static marks were observed almost all over the surface.

| Developer Composition | |
|---|---|
| Warm Water | 800 ml |
| Sodium Tetrapolyphosphate | 2.0 g |
| Anhydrous Sodium Sulfite | 50 g |
| Hydroquinone | 10 g |
| Sodium Carbonate (monohydrate) | 40 g |
| 1-Phenyl-3-pyrazolidone | 0.3 g |
| Potassium Bromide | 2.0 g |
| Water to make | 1,000 ml |
| | (pH = 10.2) |

Then, each of unexposed samples was exposed in an exposure amount of 1.6 CMS through an SP-14 Filter made by Fuji Photo Film Co., Ltd. using a tungsten lamp, developed with the above-described developer (35° C., 30 seconds), and fixed and washed with water to measure the sensitivity and fog.

Separately, these unexposed samples were stored for 3 days at 50° C., and processed in the same manner as described above to measure sensitivity and fog. Thus, the influence of the added compounds on photographic properties were examined.

Antistatic properties and the results of these tests are tabulated in the following Table 1.

TABLE 1

| Sample No. | Antistatic Agent | Remarks | Antistatic Properties Specfic Surface Resistance (ohms) | Static Mark Formation | Photographic Properties Immediately after Coating Fog | Sensi- tivity | After Storage Fog | Sensi- tivity |
|---|---|---|---|---|---|---|---|---|
| 1 | None | Control | $>1 \times 10^{14}$ | D | 0.16 | 0 | 0.16 | −0.01 |
| 2 | Compound 1 | Invention | $2 \times 10^{11}$ | A | 0.16 | 0 | 0.17 | −0.01 |
| 3 | Compound 5 | Invention | $5 \times 10^{11}$ | A | 0.16 | 0 | 0.17 | −0.02 |
| 4 | Compound 6 | Invention | $4 \times 10^{11}$ | A | 0.16 | 0 | 0.16 | −0.01 |
| 5 | Saponin | Comparison | $>1 \times 10^{14}$ | D | 0.16 | 0 | 0.17 | −0.01 |
| 6 | Saccharose Monolauric Acid Ester | Comparison | $5 \times 10^{13}$ | C | 0.16 | 0 | 0.17 | −0.02 |
| 7 | Polyoxyethylene Nonylphenyl Ether (n = 10) | Comparison | $3 \times 10^{12}$ | B | 0.15 | −0.15 | 0.24 | −0.20 |
| 8 | Polyoxyethylene Lauryl Ether (n = 20) | Comparison | $4 \times 10^{12}$ | B | 0.14 | −0.21 | 0.28 | −0.34 |

The sensitivity values in the table are presented as deviation from the standard sensitivity of control sample (sample No. 1) measured immediately after coating, in terms of the absolute value of log E. No deviation from the standard sensitivity indicates no influence on photographic properties.

As is clear from Table 1, it is seen that samples having been rendered antistatic using the compounds of the present invention scarcely suffered formation of static marks and showed an excellent antistatic effect without a detrimental influence on photographic properties. On the other hand, ordinary polyoxyethylene compounds used as comparative compounds (samples No. 7 and No. 8) seriously deteriorated photographic properties, though they improved antistatic properties to some extent.

Comparative samples (5) and (6) suffered serious formation of static marks, though influences on photographic properties were less.

Thus, it is seen that the compounds of the present invention are excellent antistatic agents showing extremely good antistatic effects without exerting influences on photographic properties.

EXAMPLE 2

A photographic emulsion prepared by adding the same stabilizer, hardener, coating aid, etc., as in Example 1 to a high speed indirect X-ray photographic emulsion containing 7 wt% gelatin and 8 wt% silver bromoiodide (AgI: 1.5 mol%) was coated on one side of an undercoated polyethylene terephthalate base. Then, a coating solution prepared by adding 10 ml of a 2% aqueous solution of 2-hydroxy-4,6-dichloro-s-triazine sodium salt as a hardener and 1 g or 0.5 g of the compound indicated in Table 2 below to 1 kg of a 2% gelatin aqueous solution was coated as a surface-protecting layer on the above-described emulsion layer, then dried to prepare samples. On the other hand, there was simultaneously prepared a sample containing a known polyoxyethylene oleyl ether (n=30) in the same amount as a comparative compound in said protective layer and a sample containing no antistatic agents (control sample) under the same conditions. The thickness of the emulsion layer and that of the protective layer were 5μ and 1μ, respectively. Specific surface resistance, degree of formation of static marks, and photographic properties of these photographic film samples were examined in the same manner as in Example 1. The results thus-obtained are shown in Table 2.

The results obtained by examining the antistatic properties of these samples in the same manner as in Example 1 are shown in Table 3.

TABLE 2

| | | | | Antistatic Properties | | Photographic Properties | | | |
| | | | | Specific | | Immediately | | | |
| | | | | Surface | Static | after Coating | | After Storage | |
| Sample | Antistatic | | | Resistance | Mark | | | | |
| No. | Agent | Remarks | Amount* | (ohm) | Formation | Fog | Sensitivity | Fog | Sensitivity |
|---|---|---|---|---|---|---|---|---|---|
| 9 | None | Control | — | $>1 \times 10^{14}$ | D | 0.15 | 0 | 0.16 | −0.01 |
| 10 | Compound 6 | Invention | 1 | $8 \times 10^{11}$ | A | 0.16 | 0 | 0.17 | −0.01 |
| 11 | Compound 9 | Invention | 0.5 | $2 \times 10^{11}$ | A | 0.15 | 0 | 0.16 | 0 |
| 12 | Polyoxyethylene Oleyl Ether (n = 30) | Comparison | 1 | $4 \times 10^{12}$ | B | 0.17 | −0.19 | 0.25 | −0.23 |
| 13 | Polyoxyethylene Oleyl Ether (n = 30) | Comparison | 0.5 | $1 \times 10^{13}$ | C | 0.16 | −0.11 | 0.20 | −0.17 |

*per 20 g solid gelatin

As is clear from Table 2, it is seen that the samples having been rendered antistatic by using the compound of the present invention suffered almost no formation of static marks and no detrimental influence on photographic properties. In addition, even the addition in lower amounts provided good results as to antistatic properties.

EXAMPLE 3

Samples 14 to 16 constructed of a backing layer, a cellulose triacetate support, an emulsion layer, and a protective layer in this order were prepared by coating and drying in a conventional manner. Formulation of each layer was as follows.

| Protective Layer | |
|---|---|
| Binder: | |
| gelatin | 1.9 g/m² |
| Hardener: | |
| 2,3-dihydroxydioxane | 1.5 g/100 g binder |
| Matting Agent: | |
| silica (mean particle size of 4 μ) | 20 mg/m² |
| Coating Aid: | |
| sodium dodecylbenzenesulfonate | 28 mg/m² |
| Emulsion Layer | |
| Binder: | |
| gelatin | 14 g/m² |
| Amount of Coated Silver: | 5 g/m² |
| Silver Halide Composition: | |
| AgI | 0.1 mol% |
| AgCl | 25 mol% |
| AgBr | 74.9 mol% |
| Antifogging Agent: | |
| 4-hydroxy-6-methyl-1,3,3a,7-tetrazaindene | 0.6 g/100 g Ag |
| Backing Layer | |
| Binder: | |
| gelatin | 0.5 g/m² |
| cellulose diacetate | 0.1 g/m² |
| Hardener: | |
| glyoxal | 1.5 g/100 g binder |
| Coating Aid: | |
| N-lauroyl-N-carboxymethyl-glycine sodium salt | 15 mg/m² |

Sample 14 comprised only the above-described composition, and samples 15 to 16 contained compounds 3 and 6, respectively, in addition to the above-described composition in the backing layer in an amount of 120 mg/m².

TABLE 3

| | | | Antistatic Properties | |
| | | | Specific | |
| | | | Surface | Static |
| Sample | Antistatic | | Resistance | Mark |
| No. | Agent | Remarks | (ohm) | Formation |
|---|---|---|---|---|
| 14 | None | Control | $>1 \times 10^{14}$ | D |
| 15 | Compound 3 | Invention | $5 \times 10^{11}$ | A |
| 16 | Compound 6 | Invention | $9 \times 10^{11}$ | A |

Table 3 reveals that the use of the compounds of the present invention serves to remarkably improve antistatic properties.

EXAMPLE 4

Samples 17, 18 and 19 constructed of a cellulose triacetate support, an antihalation layer, a red-sensitive emulsion layer, an interlayer, a green-sensitive emulsion layer, a yellow filter layer, a blue-sensitive emulsion layer, and a protective layer in this order were prepared by coating and drying in a conventional manner. The formulation of each layer is shown below.

| Antihalation Layer | |
|---|---|
| Binder: | |
| gelatin | 4.4 g/m² |
| Hardener: | |
| bis(vinylsulfonylmethyl) ether | 5 g/100 g binder |
| Coating Aid: | |
| sodium dodecylbenzenesulfonate | 4 mg/m² |
| Ingredient of Antihalation: | |
| black colloidal silver | 0.4 g/m² |
| Red-Sensitive Emulsion Layer | |
| Binder: | |
| gelatin | 7 g/m² |
| Hardener: | |
| 2-hydroxy-4,6-dichloro-s-triazine sodium salt | 0.7 g/100 g binder |
| bis(vinylsulfonylmethyl) ether | 2 g/100 g binder |
| Coating Aid: | |
| sodium dodecylbenzenesulfonate | 10 mg/m² |
| Amount of Coated Silver: | 3.1 g/m² |
| Silver Halide Composition: | |
| AgI | 2 mol% |
| AgBr | 98 mol% |
| Antifogging Agent: | |
| 4-hydroxy-6-methyl-1,3,3a,7-tetrazaindene | 0.9 g/100 g Ag |
| Color Former: | |
| 1-hydroxy-4-(2-acetylphenyl)-azo-N-[4-(2,4-di-tert-amyl-phenoxy)butyl]-2-naphthamide | 38 g/100 g Ag |
| Sensitizing Dye: | |

-continued

| | |
|---|---|
| anhydro-5,5'-dichloro-9-ethyl-3,3'-di(3-sulfopropyl)-thiacarbocyanine hydroxide pyridinium salt | 0.3 g/100 g Ag |
| Interlayer | |
| Binder: | |
| gelatin | 2.6 g/m$^2$ |
| Hardener: | |
| bis(vinylsulfonylmethyl) ether | 6 g/100 g binder |
| Coating Aid: | |
| sodium dodecylbenzenesulfonate | 12 mg/m$^2$ |
| Green-Sensitive Emulsion Layer | |
| Binder: | |
| gelatin | 6.4 g/m$^2$ |
| Hardener: | |
| 2-hydroxy-4,6-dichloro-s-triazine sodium salt | 0.7 g/100 g binder |
| bis(vinylsulfonylmethyl) ether | 2 g/100 g binder |
| Coating Aid: | |
| sodium dodecylbenzenesulfonate | 9 mg/m$^2$ |
| Amount of Coated Silver: | 2.2 g/m$^2$ |
| Composition of Silver Halide: | |
| AgI | 3.3 mol% |
| AgBr | 96.7 mol% |
| Stabilizing Agent: | |
| 4-hydroxy-6-methyl-1,3,3a,7-tetrazaindene | 0.6 g/100 g Ag |
| Color Former: | |
| 1-(2,4,6-trichlorophenyl)-3-{3-[(2,4-di-tert-amylphenoxy)-acetamido]benzamide}-4-(4-methoxyphenyl-azo)-5-pyrazolone | 37 g/100 g Ag |
| Sensitizing Dye: | |
| anhydro-5,5'-diphenyl-9-ethyl-3,3'-di(2-sulfoethyl)oxacarbocyanine anhydroxide pyridinium salt | 0.3 g/100 g Ag |
| Yellow Filter Layer | |
| Binder: | |
| gelatin | 2.3 g/m$^2$ |
| Filter Ingredient: | |
| yellow colloidal silver | 0.7 g/m$^2$ |
| Hardener: | |
| bis(vinylsulfonylmethyl) ether | 5 g/100 g binder |
| Surface Active Agent: | |
| 2-sulfonatosuccinic acid bis(2-ethylhexyl) ester sodium salt | 7 mg/m$^2$ |
| Blue-Sensitive Emulsion Layer | |
| Binder: | |
| gelatin | 7 g/m |
| Hardener: | |
| 2-hydroxy-4,6-dichloro-s-triazine sodium salt | 0.7 g/100 g binder |
| bis(vinylsulfonylmethyl) ether | 2 g/100 g binder |
| Coating Aid: | |
| sodium dodecylbenzenesulfonate | 8 mg/m$^2$ |
| Coated Silver Amount: | 2.2 g/m$^2$ |
| Silver Halide Composition: | |
| AgI | 3.3 mol% |
| AgBr | 96.7 mol% |
| Stabilizing Agent: | |
| 4-hydroxy-6-methyl-1,3,3a,7-tetrazaindene | 0.4 g/100 g Ag |
| Color Former: | |
| 2'-chloro-5'-[2-(2,4-di-tert-amylphenoxy)butyramido]-α-(5,5'-dimethyl-2,4-dioxo-3-oxazolidinyl)-α-(4-methoxybenzoyl)acetanilide | 45 g/100 g Ag |
| Protective Layer | |
| Binder: | |
| gelatin | 2 g/m$^2$ |
| styrenemaleic anhydride copolymer (1:1) having a mean polymerization degree of about 100,000 | 0.3 g/m$^2$ |
| Hardener: | |
| bis(vinylsulfonylmethyl) ether | 5 g/100 g binder |
| Coating Aid: | |

-continued

| | |
|---|---|
| sodium dioctylsulfosuccinate | 5 mg/m$^2$ |

Sample 17 comprised only the above-described composition, and samples 18 and 19 contained, in addition to the above-described composition, compound 6 and a comparative compound of polyoxyethylene lauryl ether (n=20), respectively, in an amount of 40 mg/m$^2$.

In the same manner as in Example 1 except for conducting an ordinary color development processing in place of black-and-white development processing in Example 1, antistatic properties of these samples were examined. The results thus-obtained are shown in Table 4.

TABLE 4

| | | | Antistatic Properties | |
|---|---|---|---|---|
| Sample No. | Antistatic Agent | Remarks | Specific Surface Resistance (ohm) | Static Mark Formation |
| 17 | None | Control | 1 × 10$^{14}$ | D |
| 18 | Compound 6 | Invention | 2 × 10$^{11}$ | A |
| 19 | Polyoxyethylene Lauryl Ether (n = 20) | Comparison | 5 × 10$^{12}$ | C |

As is clear from Table 4, the sample containing the compound of the present invention suffered almost no formation of static marks.

Separately, when these samples were exposed according to method of ASA No. PH-2-27-1965 and subjected to an ordinary color development processing, sample 19 containing the comparative compound suffered serious desensitization of the blue-, green- and red-sensitive layers, whereas the compound of the present invention scarcely exerted detrimental influences on photographic properties.

EXAMPLE 5

On one side of a cellulose triacetate base was coated a composition containing compound 4 and comprising the following formulation, and dried at 80° C. for 10 minutes to prepare sample 20. Also, for the purpose of comparison, comparative sample 21 was prepared in the same manner as above except for excluding the compound. Coating thickness: about 0.3μ.

| Coating Solution Formulation | Sample 20 | Sample 21 |
|---|---|---|
| Cellulose Diacetate | 0.2 g | 0.2 g |
| Water | 10 g | 10 g |
| Methanol | 50 g | 50 g |
| Acetone | 40 g | 40 g |
| Compound | 0.1 g | — |

After moisture-conditioning these samples for 5 hours at 25° C. and under 60% RH, specific surface resistance was measured under the same air conditions. Sample 21 had a surface resistance of not less than 1×10$^{13}$, whereas sample 20 containing the compound of the present invention had a surface resistance as low as 5×10$^{10}$.

EXAMPLE 6

The same light-sensitive material as sample 1 in Example 1 was prepared and, after dipping for 5 seconds in each of the 2 wt% aqueous solutions given in Table 5, air-dried under the air conditions of 25° C. and 65% RH. After moisture-conditioning for 2 hours at 25° C. and under 25% RH, specific surface resistance was measured under the same air conditions. The results thus-obtained are shown in Table 5.

TABLE 5

| Sample No. | Antistatic Agent | Remarks | Amount (g/l) | Specific Surface Resistance (ohm) |
|---|---|---|---|---|
| 22 | None | Control | — | $1 \times 10^{13}$ |
| 23 | Compound 7 | Invention | 20 | $6 \times 10^{10}$ |
| 24 | Compound 12 | Invention | 20 | $8 \times 10^{10}$ |

As is clear from Table 5, even when dip-coated as an aqueous solution, the compound of the present invention remarkably reduced the specific surface resistance, thus being effective for improving antistatic properties.

While the invention has been described in detail and with reference to specific embodiments thereof, it will be apparent to one skilled in the art that various changes and modifications can be made therein without departing from the spirit and scope thereof.

What is claimed is:

1. A photographic light-sensitive element comprising at least one silver halide emulsion layer and containing in at least one layer thereof a compound represented by the following formula:

$$R_f-O+CH_2CH_2O)_nCH_2CH_2-Y$$

wherein $R_f$ represents a perfluoroalkenyl group containing 3, 6, 9 or 12 carbon atoms, n represents an integer of 3 to 50, and Y represents a hydroxy group or an organic residue containing 1 to 18 carbon atoms, said compound being present in an amount of about 0.005 to 20 g per square meter of said element.

2. The photographic element of claim 1, wherein $R_f$ is a perfluoroalkenyl group selected from

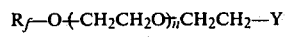

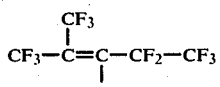

3. The photographic element of claim 1, wherein Y represents an alkoxy group, an alkenyloxy group, a phenoxy group, a naphthoxy group, an alkylphenoxy group, an alkylnaphthoxy group, an alkylamino group, an alkenylamino group, an alkylthio group, and a perfluoroalkenyl group as defined for $R_f$.

4. The photographic element of claim 1, wherein said compound is present in one or both of the outermost layers of said photographic material.

5. The photographic element of claim 4, wherein said compound is present in a surface protecting layer.

6. The photographic element of claim 4, wherein said compound is present in a backing layer.

7. The photographic element of claim 1, wherein said compound is present in an amount of about 0.001 to 0.5 g per m² of said material.

8. The photographic element of claim 1, wherein said material comprises a support having on each side thereof at least one silver halide emulsion layer and a layer containing said compound.

9. The photographic element of claim 8, wherein said photographic material is an X-ray film.

10. The photographic element of claim 1, wherein said compound is selected from the group consisting of:

 1.

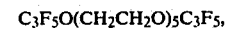 2.

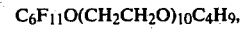 3.

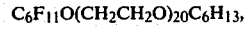 4.

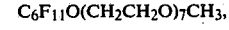 5.

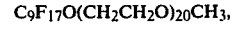 6.

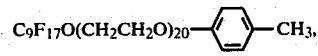 7.

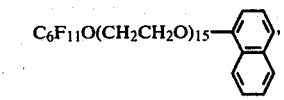 8.

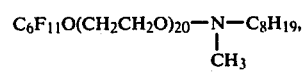 9.

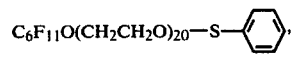 10.

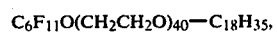 11.

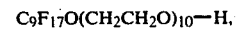 12.

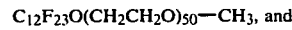 13.

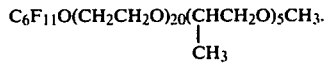 14.

* * * * *